United States Patent
Belli et al.

(10) Patent No.: US 11,675,218 B2
(45) Date of Patent: Jun. 13, 2023

(54) PAIR OF SPECTACLES WITH BIO-SENSORS

(71) Applicant: SAFILO SOCIETÀ AZIONARIA FABBRICA ITALIANA LAVORAZIONE OCCHIALI S.P.A., Padua (IT)

(72) Inventors: Nicola Belli, Padua (IT); Giorgio Manera, Padua (IT); Cristian Donà, Padua (IT); Alessandro Sanfelici, Padua (IT)

(73) Assignee: SAFILO SOCIETÀ AZIONARIA FABBRICA ITALIANA LAVORAZIONE OCCHIALI S.P.A., Padua (IT)

(*) Notice: Subject to any disclaimer, the term of this patent is extended or adjusted under 35 U.S.C. 154(b) by 344 days.

(21) Appl. No.: 16/763,626

(22) PCT Filed: Oct. 24, 2018

(86) PCT No.: PCT/IB2018/058300
§ 371 (c)(1),
(2) Date: May 13, 2020

(87) PCT Pub. No.: WO2019/097329
PCT Pub. Date: May 23, 2019

(65) Prior Publication Data
US 2020/0285080 A1 Sep. 10, 2020

(30) Foreign Application Priority Data

Nov. 16, 2017 (IT) .................. 102017000131114

(51) Int. Cl.
*G02C 11/00* (2006.01)
*G02C 5/02* (2006.01)
(Continued)

(52) U.S. Cl.
CPC ............. *G02C 11/10* (2013.01); *A61B 5/398* (2021.01); *G02C 5/02* (2013.01); *G02C 5/126* (2013.01)

(58) Field of Classification Search
CPC . G02C 11/10; G02C 5/02; G02C 5/12; G02C 11/00; A61B 5/398
(Continued)

(56) References Cited

U.S. PATENT DOCUMENTS 7,431,451 B1* 10/2008 Lin .................. G02C 5/122
                                              351/138
10,349,861 B2   7/2019 Miyazaki
(Continued)

FOREIGN PATENT DOCUMENTS

EP       1168036 A1   1/2002
EP       2668898 A1   12/2013
(Continued)

*Primary Examiner* — Thomas K Pham
*Assistant Examiner* — Henry A Duong
(74) *Attorney, Agent, or Firm* — Volpe Koenig

(57) ABSTRACT

A pair of spectacles having bio-sensors for detecting signals in contact with a user's head includes a front frame for lenses and a nose support device which is provided on the frame, the nose support device includes a mount made of an electrically non-conductive material and which can be removably connected to the frame, the mount having first and second nose support elements thereon, and which incorporate first and second nose sensors, formed from an electrically conductive material, capable of surface contact with corresponding laterally opposite zones of the nose. Each of the nose support elements is mounted on a respective support connected to the mount by a respective screw type element of a conductive material capable of electrical contact with the support, and each screw type element is capable
(Continued)

of electrical contact with an electric circuit in the frame, the circuit being interposed between the frame and the mount.

13 Claims, 9 Drawing Sheets

(51) Int. Cl.
*G02C 5/12* (2006.01)
*A61B 5/398* (2021.01)

(58) Field of Classification Search
USPC .......................................................... 351/158
See application file for complete search history.

(56) References Cited

U.S. PATENT DOCUMENTS

| | | | |
|---|---|---|---|
| 10,699,691 B1* | 6/2020 | Ye .................... | G10K 11/17881 |
| 2001/0055093 A1* | 12/2001 | Saitoh .................... | G02C 5/126 |
| | | | 351/137 |
| 2015/0148681 A1* | 5/2015 | Abreu .................. | A61B 5/6821 |
| | | | 600/474 |
| 2017/0027470 A1* | 2/2017 | Inoue ..................... | G02C 11/00 |
| 2017/0255029 A1* | 9/2017 | Klosinski, Jr. ........... | G02C 5/22 |

FOREIGN PATENT DOCUMENTS

| | | |
|---|---|---|
| EP | 3123928 A1 | 2/2017 |
| IT | 201600125471 A1 | 6/2018 |
| WO | 2016194848 A1 | 12/2016 |
| WO | 2016194853 A1 | 12/2016 |
| WO | WO-2016194848 A1 * | 12/2016 |
| WO | 2018109604 A1 | 6/2018 |

* cited by examiner

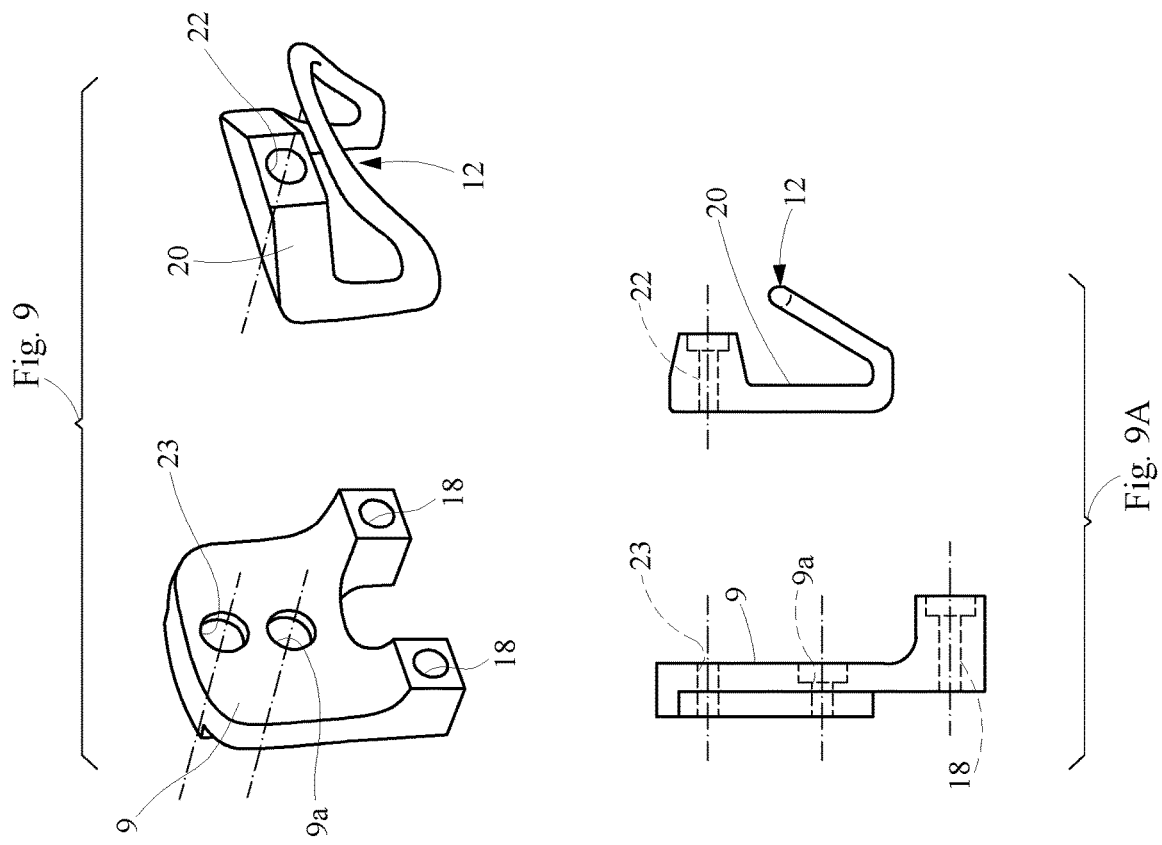
Fig. 9
Fig. 9A
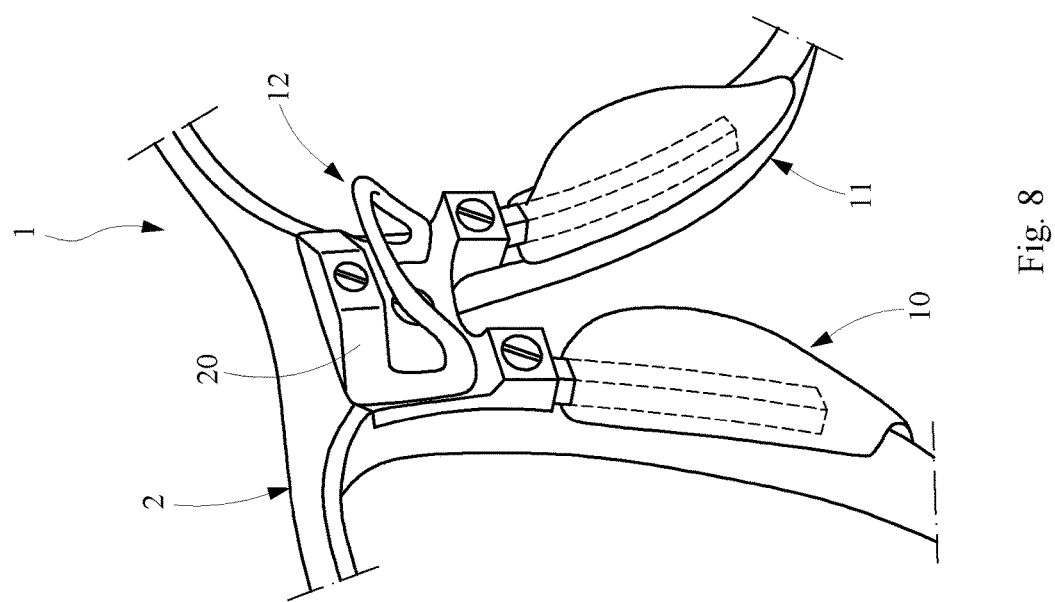
Fig. 8

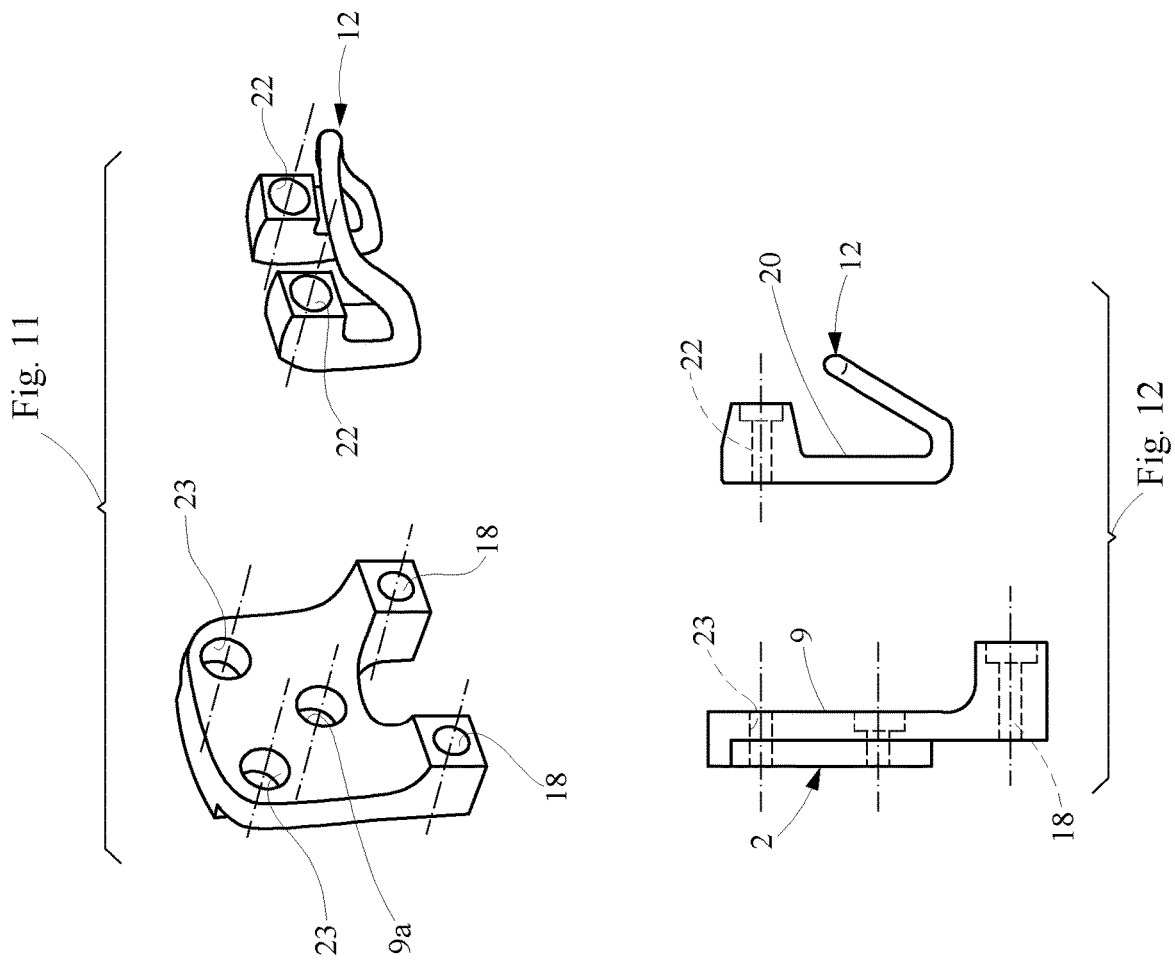
Fig. 11
Fig. 12
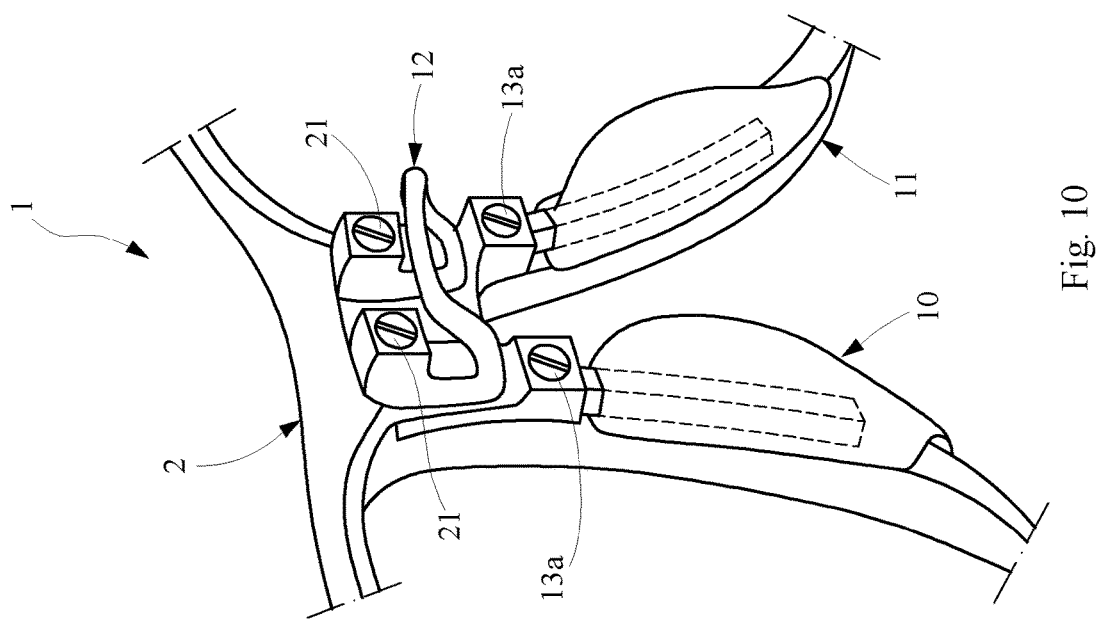
Fig. 10

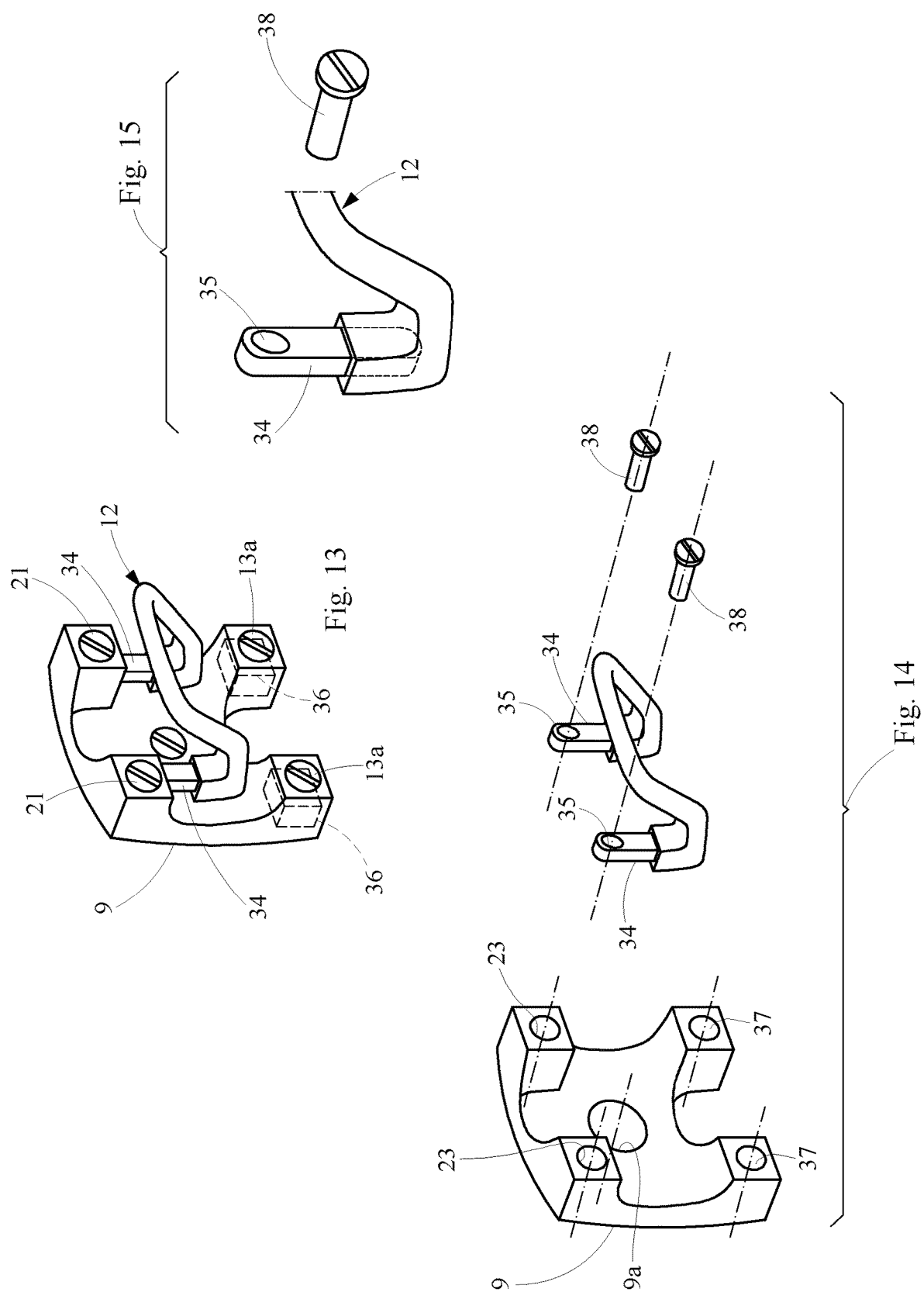

PAIR OF SPECTACLES WITH BIO-SENSORS

TECHNICAL FIELD

The present invention relates to a pair of spectacles with bio-sensors having the features set out in the appended claims.

TECHNOLOGICAL BACKGROUND

The invention is from the specific technical field of pairs of spectacles which incorporate bio-sensors in the front frame and/or on the side arms, the term "bio-sensor" being intended to be understood to be a sensor which is capable of detecting electrical signals correlating to vital functions, for example, brain functions, through the localized contact of the sensor in particular surface zones of the head.

Using such sensors on the frames for pairs of spectacles, it is possible to monitor the state of some vital functions, for example, by detecting the variation of the brain waves (electro-encephalogram), the position of the eyes (electro-oculogram), the contractions of the muscles around the eyes (electro-miogram) and the cardiac functions (electro-cardiogram).

The knowledge of the state of these functions, which can readily be acquired via the sensors which are suitably incorporated in the frame for the localized contact with the head of the user, allows an advantageous intervention in the control and monitoring of the psychological/physical states of the person, in order to optionally correct or in any case to signal situations involving risk for the health and safety of the person him/herself. Consideration is given, for example, to monitoring the states of stress and more generally fatigue which can occur during the performance of work, sporting and recreational activities.

An example of pairs of spectacles with bio-sensors is described in the Italian patent application No. 102016000125471 in the name of the same Applicant.

In the technical solution described in this patent application, there is provision for the sensors which are composed of conductive rubber and which are provided for surface contact with the face, in particular in the region of support on the nose and in the region thereabove at the root of the nose, to transfer the electrical signals detected to an electric circuit which is provided in the frame.

To this end, there is provision for all the above-mentioned sensors to transfer the respective electrical signals directly to an electric circuit which is formed as a printed circuit which is of the flexible type and which is also known in the technical sector by the term "Flex PCB" (Flexible Printed Circuit Board).

The portion of the localized circuit in the region of the central bridge for support on the nose is arranged in a position under the central mount which carries the sensors and which is connected in a removable manner to the front of the frame, the circuit being in this manner interposed between the sensors and the front of the frame.

In order to ensure a suitable acquisition of the signal, it is required that the circuit extend over quite an extensive area, which extends from the upper zone of the root of the nose as far as the lower zones of the nose support plates.

SUMMARY

A main object of the invention is to provide pairs of spectacles which are provided with bio-sensors which are structurally and functionally configured to improve the technical solutions currently known, in particular connected with the problems relating to the transfer of the signals acquired by the sensors, which are provided in the central nose support portion of the frame, to the electric circuit which is provided in the frame, in order to obtain an improved constructive simplification of the components involved, at the same time ensuring suitable reliability and efficiency thereof.

This object and other objects which will be set out below are achieved by the invention by means of pairs of spectacles with bio-sensors which are constructed in accordance with the appended claims.

BRIEF DESCRIPTION OF THE DRAWINGS

The features and advantages of the invention will be better appreciated from the following detailed description of some of the preferred embodiments thereof which are illustrated, by way of non-limiting example, with reference to the appended drawings, in which:

FIG. 8 is a view corresponding to that of FIG. 7 in a construction variant of the detail depicted, FIG. 9 is a perspective view, with disconnected portions, of a detail of the pair of spectacles of FIG. 8, FIG. 9A is a side view of the detail of FIG. 9, FIG. 10 is a view corresponding to that of FIG. 7 in relation to another construction variant of the detail shown, FIG. 11 is a perspective view, with disconnected portions, of a detail of the construction variant of FIG. 10, FIG. 12 is a side view of the detail of FIG. 11, FIG. 13 is a perspective view, in an assembled condition, of another construction variant of the detail of FIG. 11, FIG. 14 is an exploded perspective view of the detail of FIG. 13, FIG. 15 is a partial, perspective view, to an enlarged scale, of a detail of FIG. 14.

DETAILED DESCRIPTION OF THE PREFERRED EMBODIMENTS

Figure 1:
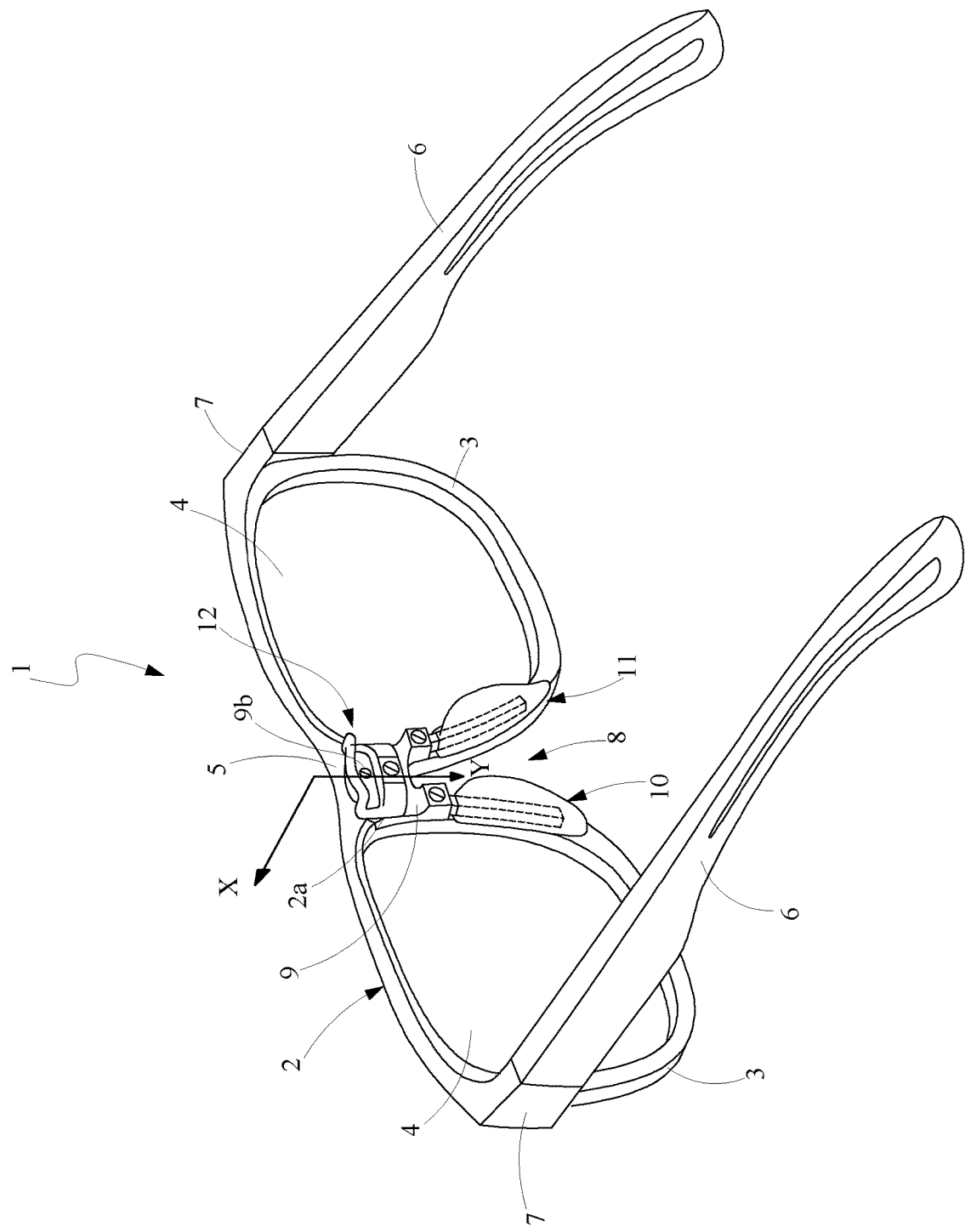
FIG. 1 is a perspective view of an example of a pair of spectacles according to the present invention.
Figure 2:
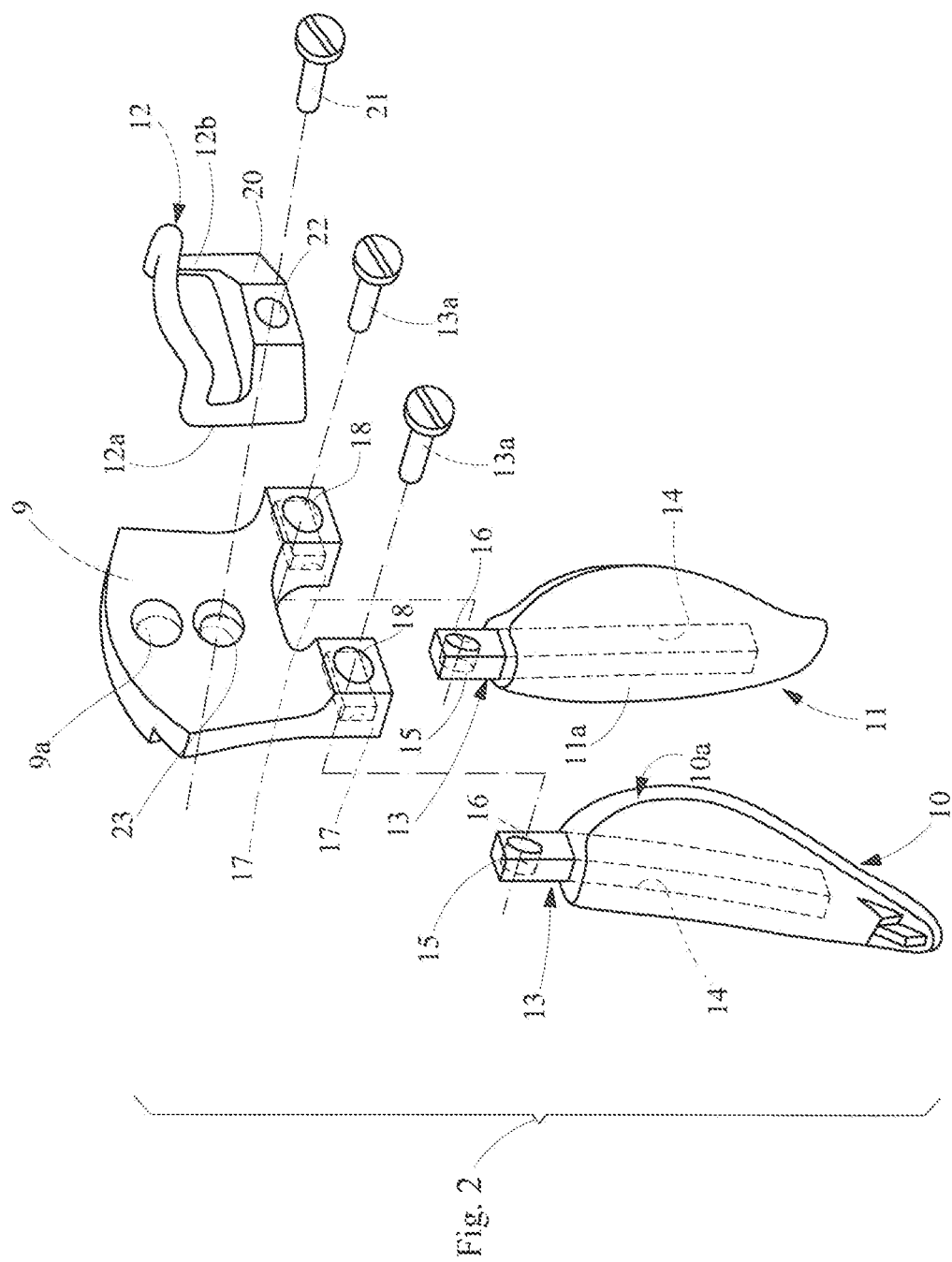
FIG. 2 is an exploded perspective view to an enlarged scale of a detail of the pair of spectacles of FIG. 1.
Figure 5:
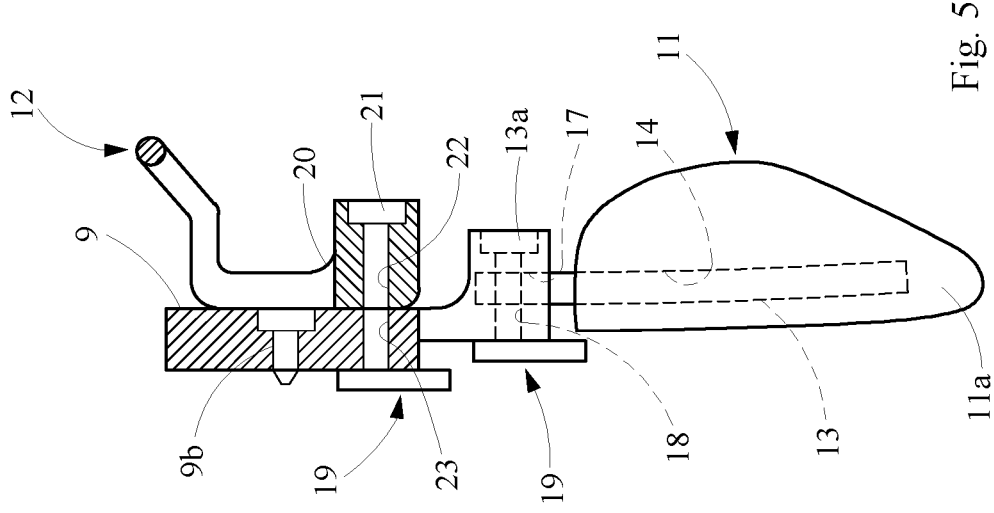
FIG. 5 is a partially sectioned side view, to an enlarged scale, of the detail of FIG. 2 in an assembled state.
Figure 4:
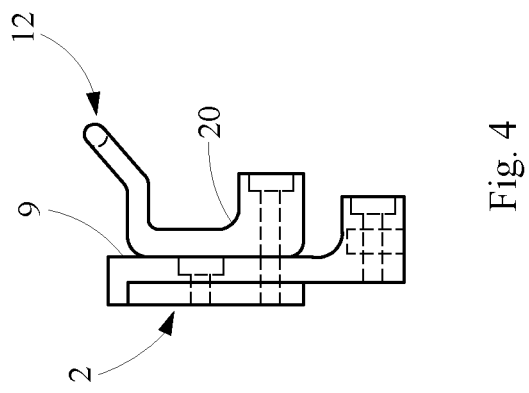
FIG. 4 is a side view of the components of the detail of FIG. 3 in a connected state.
Figure 3:
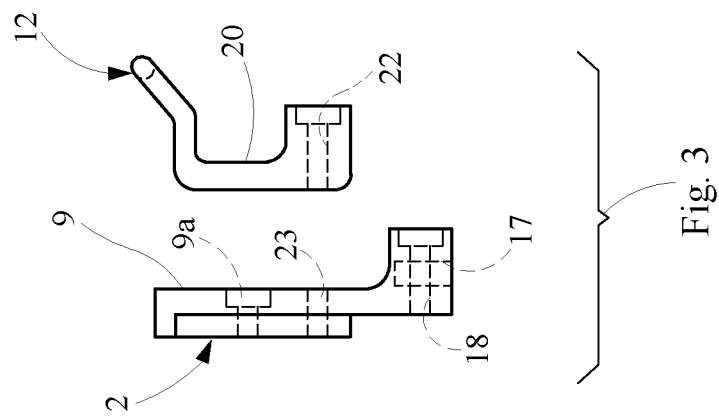
FIG. 3 is a side view, with disconnected portions, of a pair of components of the detail of FIG. 2.

Initially with reference to FIGS. 1 to 9, there is generally designated 1 a first embodiment of a pair of spectacles with bio-sensors, constructed according to the present invention.

The pair of spectacles comprises a front frame 2 with a pair of respective rims 3 for supporting corresponding lenses 4, which are mutually connected centrally by a bridge 5 which extends in the nose region. There are designated 6 both the side arms of the pair of spectacles which are articulated, in a hinging manner, to respective lugs 7 which are provided on the frame 2 at laterally opposite sides thereof.

The pair of spectacles is provided with bio-sensors which are located in the central region of the frame which is suitable for support on the nose and which can be further provided with sensors in the rear zone of the ear, where the support of the side arms on the head of the user takes place, the present invention not, however, relating to the provision of bio-sensors on the side arms.

The term "bio-sensor" is intended to be understood to refer in the present context to a sensor which is configured to detect electrical signals which correlate to the vital functions of the person, such as, for example, brain waves, the heartbeat or other vital parameters.

Therefore, the above-mentioned sensors are functionally configured as electrodes which are intended for contact with the skin, in order to detect the electrical signal and to transfer it by means of a system of conductors of electrical signals which is provided in the frame, to an electronic module which is provided with a circuit complex which is suitable for administering the signals detected.

For any detail or specific feature which is not expressly described or indicated below, the content of the prior Italian patent application No. 102016000125471, in the name of the same Applicant, is incorporated by reference in its entirety herein as if fully set forth.

The pair of spectacles is provided with a nose support device 8 which comprises a mount 9 which is structurally independent of the front frame 2 and which can be connected in a removable manner to the frame itself.

There are provided on the mount 9 a first and a second nose support element 10, 11 which are opposite each other and each of which incorporates a first nose sensor and second nose sensor 10*a*, 11*a*, respectively, which are capable of surface contact with corresponding laterally opposite zones of the nose.

A third sensor which is designated 12 is provided centrally on the mount 9, above the sensors 10*a*, 11*a*, and in a position spaced apart from the sensors so as to come into surface contact with the face in the region of the root of the nose, slightly below the "glabella" of the head, with the pair of spectacles being worn.

The sensors 10*a*, 11*a* and 12 are advantageously formed from a resiliently flexible and electrically conductive material, for example, from an elastomer material or rubber with properties of electrical conductivity, in order, on the one hand, to ensure comfort and adaptability of fit during supporting contact and, on the other hand, to perform the function of an electrode for detecting respective signals by the sensor.

The mount 9 having a plate-like configuration is produced from an electrically non-conductive material and has a through-hole 9*a* for engaging with a clamping screw 9*b* which is intended to clamp the mount to the front frame 2 at the inner side thereof, that is to say, the side directed towards the face when the pair of spectacles is being worn.

A recess 2*a* is provided in the frame 2 in the region of the bridge 5 and over a part of the rim portions 3 it extends under the bridge. The recess 2*a* is obtained as a surface indentation of the corresponding mounting zone and has such a formation as to receive in a coupling manner the mount 9, as shown in FIG. 1. The mount is fixed by means of engagement of the clamping screw 9*b* in the frame, extending through the hole 9*a*.

Each of the nose support elements 10, 11 is mounted on a respective support 13 of electrically conductive material, which is connected to the mount by means of a respective screw type element 13*a*.

The supports 13 are specularly symmetrical with respect to a central plane of symmetry which is defined by the lines of axis X and Y in FIG. 1, as a result of the symmetry only one of the supports 13 will be described in detail.

Each support 13 is produced in the form of a rod-like core which is electrically conductive and which is surrounded for the most part of the extent thereof inside the corresponding nose support element 10, 11.

As clearly shown in the Figures, each nose support element 10, 11 which incorporates the corresponding sensor is formed as a "nose plate" for comfortable support on the sides of the nose and has a respective tubular recess 14 for receiving, with relative fixing, the corresponding rod-like support 13. The rod-like support 13 comprises, in the region of an end portion 15 thereof, projecting from the corresponding tubular recess 14, a through-hole 16. The end portion 15 is formed in order to engage with substantial form-fitting connection with a respective recess 17 which is formed in the mount 9. Each recess 17 is transversely intersected by a respective through-hole 18 through the thickness of the plate-like mount 9. Each hole 18 is internally threaded for screw type engagement with the corresponding screw type element 13*a*.

Each screw type element 13*a* is capable of engaging with respective holes 16 and 18 which are arranged to be coaxial relative to each other following the engagement of the support portion 15 in the recess 18 by connecting the support 13 to the mount 9.

Following this connection, the screw type element 13*a* is capable of electrical contact by means of the free end thereof opposite the head of the screw, with an electric circuit 19 which is provided in the frame for transferring the electrical signals.

Advantageously, the electric circuit 19 is produced as a flexible printed circuit board also known in the field referred to using the term "flex PCB".

The circuit 19 is partially received inside the front of the frame 2 (the one involved by the upper portions of the lens-carrying rims 3 which extend over the region of the eyebrow arch) and partially inside the hinge zone between the arm and lug, extending until it reaches a location inside housings (not illustrated) which are provided on one or both side arm(s).

In order to receive the circuit 19 on the frame, the frame is provided with respective seats which are formed on the rims 3 and the lugs 7, at the inner side of the frame, the seats optionally being connected to respective closure inserts so as to hide from view the circuit 19 which extends over the frame portion.

Figure 6:
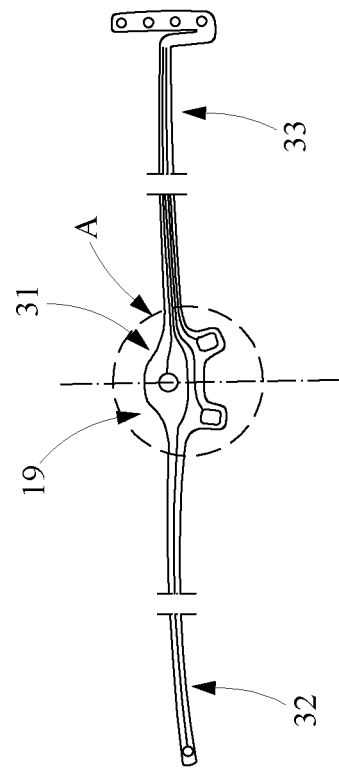
FIG. 6 is a schematic view of a printed electric circuit which can be connected to the frame of the pairs of spectacles of the invention.

FIG. 6 shows a partial schematic illustration, with a planar extent, of an example of a circuit 19 which extends from the opposite lateral ends (associated with the arms 6), extending through the lens-carrying rims 3, as far as the region of the central bridge 5, where the area of electrical contact with the screw 13*a* is concentrated.

Since the electric circuit 19 remains interposed between the frame front 2 and the mount 9, the electrical signals are transferred from the respective sensor 10*a*, 11*a* to the circuit 19, exclusively via the respective screw type element 13*a* which therefore closes the electrical contact between the corresponding sensor and the electric circuit.

Advantageously, the electrical contact between each screw type element 13a and the corresponding support 13 is brought about between the internal peripheral surface of the hole 16 and the external surface of the shank of the screw 13 which engages with the hole 16. As a result of the configuration above, the extent of the frame front which requires coverage with a flex PCB circuit (suitable for receiving the electrical signal transferred via the nose plates) is reduced because it is sufficient for it to be limited to the zone of the respective plate in which the fixing with respect to the screw 13a takes place, exclusively the screw closing the electrical contact with the circuit. A simplified construction connected with the reduced surface extent required by the flex PCB circuit is thereby obtained.

The third sensor 12 (also indicated as the "glabella sensor") extends in a bridge-like manner over the nose support elements 10, 11 remaining spaced apart from the mount 9 (projecting towards the face with the pair of spectacles being worn) in order to ensure the support contact thereof with the zone of the root of the nose, the sensor 12 being further fixedly joined at the opposite ends 12a, 12b thereof to a respective support 20, the support 20 in turn being intended to be connected to the mount 9 in a removable manner.

The support 20 which is produced from electrically conductive material is connected in a removable manner to the mount 9 by means of a respective screw type element 21 which is also produced from a conductive material and which is capable of electrical contact with the electric circuit 19.

In greater detail, the support 20 and the mount 9 have respective through-holes 22, 23 which are capable of relative coaxial alignment so that the screw type element 21 can lock, by means of engagement in the holes 22, 23, the support 20 to the mount 9, ensuring at the same time the electrical contact between the sensor 12 and the electric circuit 19. For locking the support 20 to the mount 9, there is provision for the hole 23 in the mount to be internally threaded in order to receive the threaded shank of the screw type element 21 with threaded engagement.

Since the electric circuit also remains interposed in this case between the front of the frame 2 and the mount 9, the electrical signals are transferred by the respective sensor 12 to the circuit 19, exclusively via the respective screw type element 21 which closes the electrical contact between the corresponding sensor and the electric circuit. The electrical contact between the screw 21 and the support 20 is produced by means of the surface contact between the internal surface profile of the hole 22 and the threaded shank of the screw which extends through it.

Figure 7:
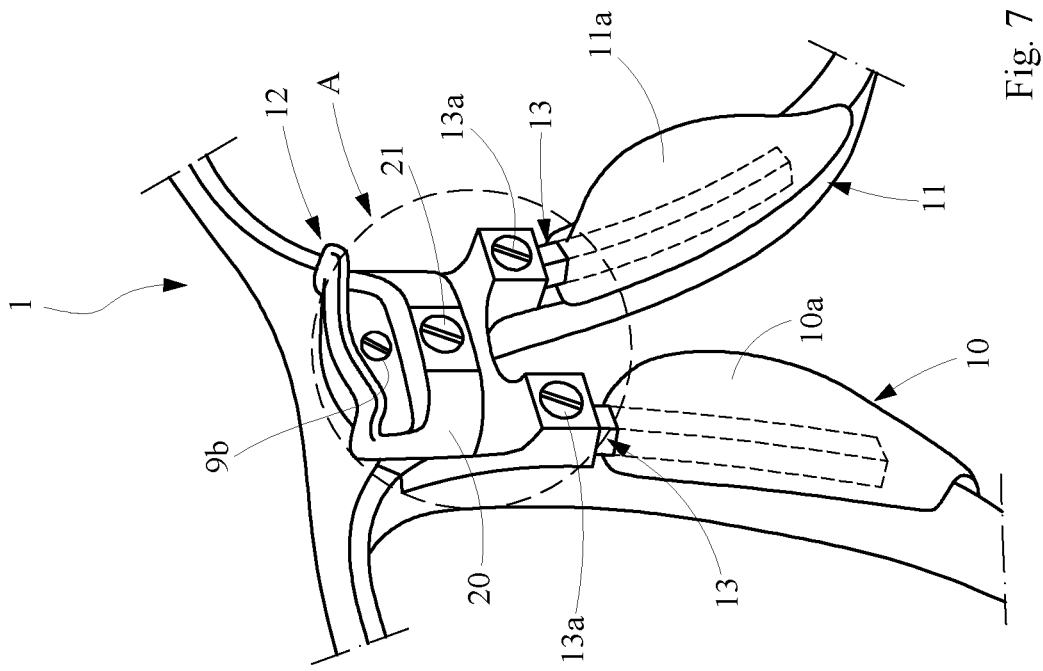
FIG. 7 is another partial, perspective view of a detail of the pair of spectacles of FIG. 1.

FIG. 7 shows, in a manner schematically surrounded by a circular perimeter (indicated by the arrow A), the area of the front of the frame in which the cover is located with a flex PCB circuit 19 in order to receive the signals of sensors 10a, 11a and 12, this area being substantially reduced as a result of the simplified construction which provides for positioning the pair of screws 13a (for the sensors 10a, 11a) and the screw 21 (for the sensor 12) nearer each other, with a resultant reduction of the extent of the flex PCB circuit.

Again with reference to FIG. 6, there is defined in the flex PCB circuit 19 a central zone 31 which is intended for the electrical connection of the sensors 10a, 11a and 12 of the nose support device, from which there extend, at opposite sides, two respective conductive lines 32 and 33, the line 32 being directed along one of the side arms (for example, directed to an electrical supply battery which is received in the arm), the line 33 being directed instead along the other arm (for example, in the direction of an electronic module received in the arm).

The central zone 31 is the portion of the circuit which is intended to be interposed between the recess 2a of the frame which receives the mount 9 and the mount 9 itself. In order to ensure the electrical contact, respective zones which are covered with electrically conductive material (for example, of gold), may be provided for direct contact, respectively, with the pair of screws 13a and with the screw 21. Conductive tracks which are only partially illustrated in FIG. 7 are integrated in the circuit for conducting the electrical signals, which are advantageously insulated from each other.

With regard to the materials which can be used for producing the mount 9, various types of plastics materials are advantageously suitable for the purpose. By way of non-limiting example, mention may be made of the plastics materials based on polyamides (including the material commercially known as "Grilamid® TR90") or the plastics materials based on polypropylene.

Also with regard to the construction of the front and the arms, there may advantageously be used various types of plastics materials, including the same materials mentioned for the possible construction of the mount 9.

For the optional increase of the superficial electrical conductivity of the bio-sensor of conductive elastomer material, it is possible to provide for the use of electrically conductive coatings, for example, with inks or paints which are electrically conductive. With regard to the housings provided in one or both of the arms, to which, however, the present invention does not relate, they may be of different construction types.

In one embodiment, the housing on one of the arms is intended to receive the electronic module while the housing constructed on the other arm is intended to receive a battery for the electrical supply of the electronic module and the sensors. The battery is preferably of the rechargeable, non-removable type. Alternatively, it may also be of the removable type. It may further be of the non-rechargeable type and, in this case, it will have to be necessarily removable in order to be able to be replaced once it has become discharged.

Other configurations are possible in any case. There may further be provision for one or other housing of the corresponding arms to be intended to receive, additionally or alternatively to the electronic module or the battery, other devices or components which are suitable for controlling or transmitting the signals detected by the sensors.

With reference to FIGS. 8, 9 and 9A, in a first construction variant of the sensor 12, there is provision for the bridge type sensor to be arranged under the support 20 with which it is fixed to the mount 9. As a result, the hole 9a in the mount 9 is provided in a position between the upper hole 23 and the pair of lower holes 18.

In another construction variant of the sensor 12, illustrated in FIGS. 10 to 12, there are provided a pair of screws 21 for fixing the sensor to the mount 9, the screws producing two different contact points with respect to the electric circuit 19, thereby increasing the overall electrical contact surface for the transfer of the signals acquired by the sensor via the screws.

In another construction variant of the preceding embodiment, with reference to FIGS. 13 to 15 there is provision for the opposite lateral ends of the sensor 12 to be fixedly joined to respective electrically conductive extension pieces 34 which are in turn fixedly joined to the mount 9 with the same method described in the preceding examples for connecting the supports 13 to the mount 9. To this end, the portion of each extension piece 34 which projects from the end of the sensor 12 is provided with a through-hole 35 and is capable of engaging, at least partially, with a respective blind seat 36 which is provided in the mount 9. Each of the recesses 36 is intersected transversely by a respective through-hole 37. The holes 35 and 36 which are brought into coaxial alignment with each other (by means of engagement of the extension piece 34 in the seat 36) are capable of being engaged by a respective screw 38 which is produced from electrically conductive material and which is provided for fixing the sensor 12 to the mount 9 and for closing the electrical contact with the circuit 19.

By the extension pieces 34 being produced from ductile metal material, it is possible to produce a recording of the positioning of the sensor 12 by means of deformation of the extension pieces in predetermined directions (for example, via an inclination of the sensor upwards or downwards).

In this case, there is also provision for the electrical contact to be carried out between the external surface of the shank of the corresponding screw 21 and the internal surface of the hole 35 provided in the respective extension piece 34.

It is also possible to provide a sensor 12 which extends in a bridge-like manner on the mount with a single extension piece 34 which extends from one end of the sensor to the other.

Figure 17:
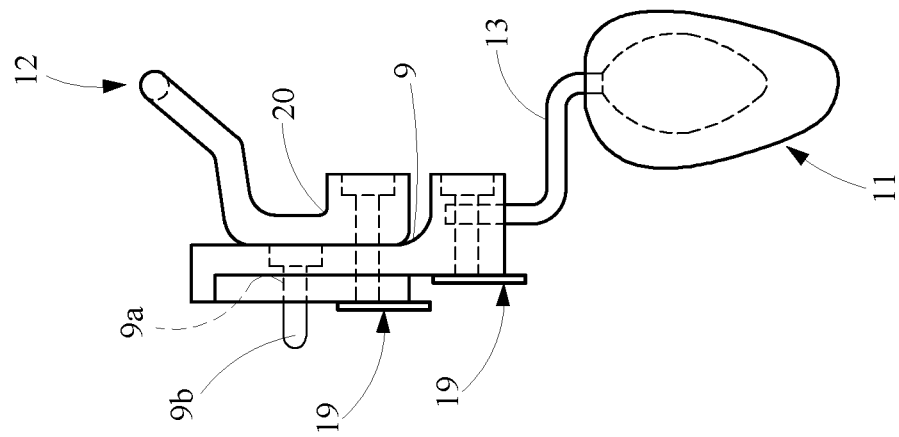
FIG. 17 is a side view of the detail of FIG. 16.
Figure 16:
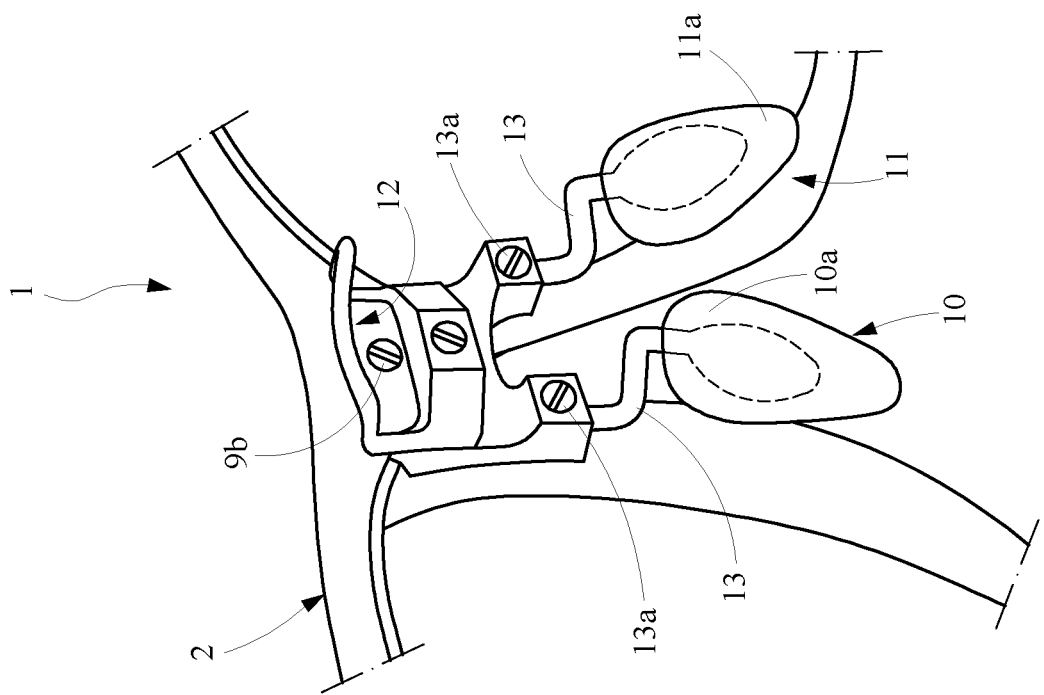
FIG. 16 is a view corresponding to that of FIG. 7 in relation to another construction variant of the detail shown.

In an embodiment, with reference to FIGS. 16 and 17 there is provision for the nose support elements 10, 11 to be produced as sensor plates which are arranged in a position spaced apart from the respective rim of the front of the frame. To this end, the supports 13 can be configured with a filiform structure (for example, from metal wire), at one end of which there is fixedly joined a sensor plate for the nose support. At the end, there may be provided a structure which is suitable for ensuring the connection between the wire itself and the sensor plate, this structure being, for example, of disk-like form or plate-like form having dimensions less than those of the sensor plate, and constructed from metal and welded to the wire. In this manner, the sensor plate can be advantageously connected to the wire by means of an injection-molding process (also known as "insert molding"), that is to say, co-injecting the plate around the disk (or internal plate).

Similarly, at the opposite end of the filiform structure there may be provided a structure which is suitable for allowing the stable connection of the support 13 to the corresponding recess 17 which is formed in the mount 9. This connection structure (not illustrated) can be constituted, for example, by a plate which has a width greater than the diameter of the metal wire produced from conductive metal material, welded to the end of the metal wire itself, and provided with a through-hole (similar to the through-hole 16 provided in the support 15 of the construction examples described above) which is capable of being engaged by the screw 13a, coaxially with the hole 18 of the mount 9. The plate is formed to engage, with substantial form-fitting connection, with the recess 17 which is formed in the mount 9.

As a result of the configuration of this construction variant, the position of each of the sensor plates for the nose support can be subjected to recording. Furthermore, the adaptability of fit of the sensors 10a, 11a being ensured by the deformability of the supports 13 of ductile material, it is possible to construct the sensor plates from a conductive plastics material of the rigid type, as an alternative to the use of conductive rubber.

Figure 18:
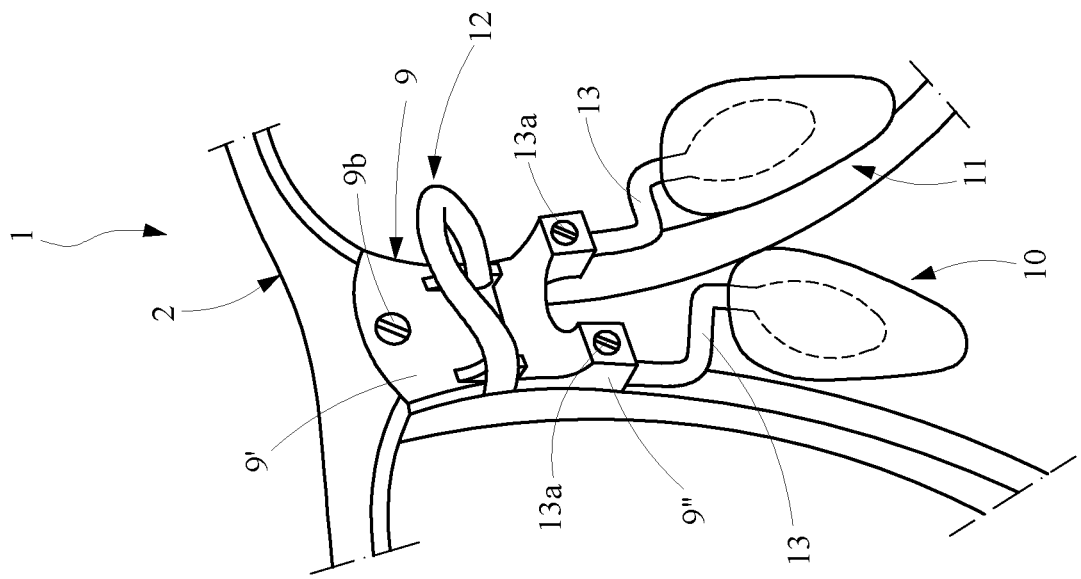
FIG. 18 is a view corresponding to that of FIG. 16 in relation to another construction variant of the detail shown.
Figure 20:
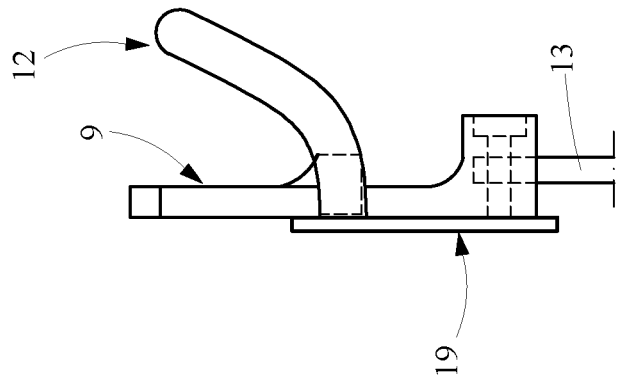
FIG. 20 is a partial side view of the detail of FIG. 18.
Figure 19:
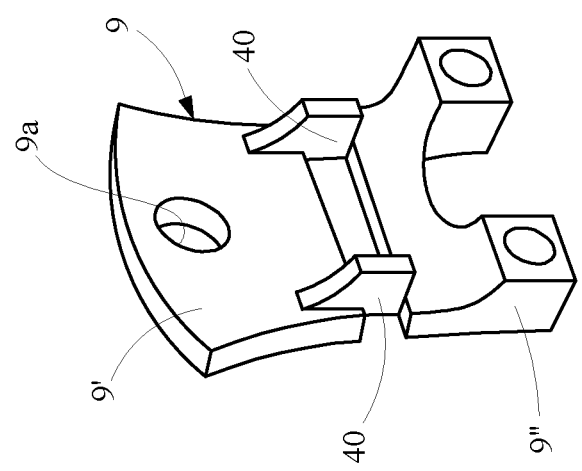
FIG. 19 is a perspective view of a component of the detail of FIG. 18.

In an embodiment, with reference to FIGS. 18 to 20 there is provision for the sensor 12 of the nose support device to be produced as a structure with a central bridge from conductive rubber which is injection-molded over the support mount 9 composed of non-conductive plastics material.

To this end, the mount 9 comprises an upper portion 9' and a lower portion 9" which are connected to each other by means of a pair of connection arms 40 which are mutually spaced apart.

These arms 40 produce the support structures for the two opposing ends 12a, 12b of the bridge-like sensor 12. By means of the injection-molding process, the bridge-like sensor is injection-molded in such a manner that the two ends 12a, 12b wrap round the respective arms 40 with mutual connection.

There are further mounted on the mount 9 a pair of nose sensor plates 10a, 11a which are composed of conductive rubber or plastics material and which are formed with the structure of the embodiments previously described (for example, as shown in FIG. 16). Therefore, there is provision for the use of cores or conductive metal extension pieces for connecting each nose plate to the support mount.

Furthermore, the plates are fixed to the support mount by means of respective screws which are further used for transmitting the electrical signal.

As shown in FIG. 20, the electrical circuit 19 of the flex PCB type is in electrical contact with the bridge-like sensor 12 (which is injection-molded on the mount) and with the screws 13a for electrical conduction connected to the extension pieces 34 of the sensor plates.

Advantageously, this variant combines the construction simplicity of the central/upper portion (bridge-like sensor), if obtained by means of over-molding of (conductive) rubber on plastics material (non-conductive), with the possibility of obtaining nose sensor plates which can be recorded by using electrically conductive extension pieces (composed of a ductile material) and using screws which are also electrically conductive.

The invention achieves the objects set out affording the advantages set out with respect to the known solutions.

The invention claimed is:

1. A pair of spectacles provided with bio-sensors for detecting signals in contact with a user's head, the spectacles comprising a front frame (2) for supporting respective lenses (4) and a nose support device (8) which is provided on the frame, the nose support device comprising a mount (9), which is produced from an electrically non-conductive material and which can be connected in a removable manner to the frame (2), the mount comprising thereon a first and a second nose support element (10, 11) which are opposite each other and which incorporate a first nose sensor and second nose sensor (10a, 11a) which are formed from an electrically conductive material and which are capable of surface contact with corresponding laterally opposite zones of the nose, each of the first and second nose support elements (10, 11) is mounted on a respective support (13) of an electrically conductive material, which is connected to the mount (9) by a respective screw typo element (13a) of a conductive material which is capable of electrical contact with the support (13), each screw element (13a) is capable of electrical contact with an electric circuit (19) which is provided in the frame (2) for transferring the electrical signals detected by the corresponding sensors (10a, 11a), the circuit (19) being interposed between the frame (2) and the mount (9), so that the electrical signals are transferred from the respective sensor (10a, 11a) to the electric circuit (19), via the respective screw element (13a) which is capable of closing the electrical contact between the corresponding sensor and the electric circuit, wherein each of the supports (13) comprises in an end portion (15) region thereof a first through-hole (16) for engaging in a recess (17) which is formed in the mount (9), the electrical contact between each screw element (13a) and the corresponding support (13) being brought about between an internal surface of the first through-hole (16) and an external surface of the screw element (13a) which engages with the first through-hole, and wherein the screw element is capable of electrical contact by means of a free end thereof opposite a head of the screw element, with the electric circuit (19).

2. The pair of spectacles according to claim 1, wherein the recess (17) is transversely intersected by a second through-hole (18) in the mount, the corresponding screw element (13a) being capable of engaging with the first through-hole and second through-hole (16, 18), which are coaxial with each other following the engagement of the support portion (15) in the recess (17), for connecting the support (13) to the mount (9) and the electrical contact of the screw element (13a) with the circuit (19).

3. The pair of spectacles according to claim 1, wherein the first and second nose support elements (10, 11) are formed from conductive rubber or plastics material.

4. The pair of spectacles according to claim 1, wherein the supports (13) are received in respective tubular recesses (14) which are formed in the respective first and second nose support elements (10, 11).

5. The pair of spectacles according to claim 1, wherein the nose support elements (10, 11) are formed from rigid conductive plastics material and the supports (13) are formed from a ductile metal material so that the positioning of the support elements can be recorded by means of deformations of the supports.

6. The pair of spectacles according to claim 1, further comprising a third sensor (12) which is mounted centrally on the mount (9), which is formed from an electrically conductive material and which is arranged in a position spaced apart from the first and second sensors (10a, 11a), for surface contact with the face in the region of the zone of the root of the nose.

7. The pair of spectacles according to claim 6, wherein the third sensor (12) is provided on a respective third support (20) which is produced from an electrically conductive material, which is connected to the mount (9) by means of a respective third screw element (21; 38) of a conductive material which is capable of electrical contact with the third support, the third screw element (21; 38) further being capable of electrical contact with the electric circuit (19) which is provided in the frame for transferring the electrical signals which are detected by the sensors, so that the electrical signals are transferred from the respective third sensor (12) to the electric circuit (19) by means of the respective third screw element (21; 38) which is capable of closing the electrical contact between the corresponding third sensor (12) and the electric circuit (19).

8. The pair of spectacles according to claim 7, wherein the support (20) for the third sensor (12) and the mount (9) have at least a third through-hole (22; 35) and a fourth through-hole (23) which are capable of relative coaxial alignment for engaging with the respective third screw element (21; 38) of an electrically conductive material, respectively.

9. The pair of spectacles according to claim 8, wherein the third support (20) comprises at least one pair of extension pieces (34) which are connected to opposing lateral ends of the third sensor (12), the extension pieces (34) being formed from an electrically conductive and ductile metal material, each of the ends having the third hole (35) and being capable of at least partially engaging with a respective seat which is formed in the mount (9) in order to coaxially align the third hole with the fourth hole, for engaging with the corresponding third screw element (21; 38), the positioning of the third sensor (12) being recordable to a limited extent by means of deformation of the extension pieces (34).

10. The pair of spectacles according to claim 9, wherein the electrical contact between each extension piece (34) and the corresponding screw element (21; 38) is produced between an internal peripheral surface of the third hole and the external surface of the screw element which engages with the third hole.

11. The pair of spectacles according to claim 6, wherein the third sensor (12) is formed from a conductive rubber which is over molded on a portion of the mount (9) and which is capable of electrical contact with the electric circuit (19).

12. The pair of spectacles according to claim 11, wherein the mount (9) comprises an upper mount portion (9') and a lower mount portion (9") which are connected to each other by a pair of connection arms (40), the upper portion having a hole (9a) for a screw connection of the mount to the frame, the lower portion having the through-holes for the connection of the nose support elements (10, 11) which incorporate the first and second nose sensors, the third sensor (12) being injection—molded over the mount so as to wrap round the arms (40) with the opposite lateral ends thereof and to ensure the electrical contact with the electric circuit (19) which is interposed between the frame and the mount.

13. The pair of spectacles according to claim 1, wherein the electric circuit (19) is configured as a flexible printed circuit board.

\* \* \* \* \*

UNITED STATES PATENT AND TRADEMARK OFFICE
CERTIFICATE OF CORRECTION

PATENT NO. : 11,675,218 B2
APPLICATION NO. : 16/763626
DATED : June 13, 2023
INVENTOR(S) : Nicola Belli et al.

Page 1 of 1

It is certified that error appears in the above-identified patent and that said Letters Patent is hereby corrected as shown below:

In the Claims

In Claim 1, at Column 8, Line 58, after the word "screw", delete the word "typo".

Signed and Sealed this
Twenty-fifth Day of July, 2023

Katherine Kelly Vidal
*Director of the United States Patent and Trademark Office*